US007090196B1

(12) United States Patent
Linker

(10) Patent No.: US 7,090,196 B1
(45) Date of Patent: Aug. 15, 2006

(54) METHOD OF REMOVING A STUN GUN DART

(76) Inventor: Carson R. Linker, 9515 NE. 312th Ave., Camas, WA (US) 98607

( * ) Notice: Subject to any disclaimer, the term of this patent is extended or adjusted under 35 U.S.C. 154(b) by 0 days.

(21) Appl. No.: 10/909,704

(22) Filed: Aug. 2, 2004

(51) Int. Cl.
*A61M 5/00* (2006.01)

(52) U.S. Cl. .......................................... 254/1; 604/263

(58) Field of Classification Search ................ 119/174; 73/167, 102, 501, 506, 512, 513; 43/6; 273/108; 81/25; 604/130, 263; 473/578, 581, 585, 473/586; 29/263, 256, 264; 254/18, 19, 254/20, 25, 1; 606/1
See application file for complete search history.

(56) References Cited

U.S. PATENT DOCUMENTS 1,133,124 A * 3/1915 Geratt ...................... 30/308.3
1,381,683 A * 6/1921 Weinbeer ..................... 254/22
1,387,582 A * 8/1921 Bergamini ................ 254/26 R
1,807,347 A * 5/1931 Schweigert .................... 81/25
2,620,190 A * 12/1952 Bean .......................... 473/585
2,706,103 A * 4/1955 Stambaugh et al. .......... 254/19
3,314,286 A * 4/1967 Hickerson et al. ............ 73/167
3,457,921 A * 7/1969 Waldeisen .................. 604/130
3,629,883 A * 12/1971 Norman ......................... 7/170
4,043,020 A * 8/1977 Hoggard .................... 29/426.5
4,103,893 A * 8/1978 Walker ....................... 473/581
4,150,469 A * 4/1979 Hoggard ...................... 29/254
4,174,837 A * 11/1979 Benke ........................ 473/581
4,182,327 A * 1/1980 Haley ......................... 604/130
4,584,983 A * 4/1986 Ament ........................ 124/89
4,684,366 A * 8/1987 Denny et al. ............... 604/130
4,735,612 A * 4/1988 Chevalier ................... 604/130
5,068,954 A * 12/1991 Houska ....................... 29/240
5,141,205 A * 8/1992 Iwai et al. .................... 254/18
5,205,193 A * 4/1993 Wield ...................... 81/176.15
5,255,575 A * 10/1993 Williams ....................... 81/25
5,381,976 A * 1/1995 Chon et al. ................. 241/197
5,437,641 A * 8/1995 Cameron .................... 604/130
5,495,630 A * 3/1996 Estein et al. ................... 7/138
5,526,719 A * 6/1996 Chen ............................ 81/25
5,566,924 A * 10/1996 Shirk .......................... 254/18
5,603,506 A * 2/1997 Pickup ....................... 473/585
5,682,660 A * 11/1997 Hansen ........................ 29/264
5,797,927 A * 8/1998 Yoon .......................... 606/144
5,797,954 A * 8/1998 Shaffer et al. .............. 606/201
5,836,842 A * 11/1998 McLearan ................... 473/581
5,897,563 A * 4/1999 Yoon et al. ................. 606/144
6,767,003 B1 * 7/2004 Toensing ..................... 254/25
6,869,374 B1 * 3/2005 Lane .......................... 473/578
2002/0049414 A1 * 4/2002 Nobles et al. .............. 604/187
2002/0095122 A1 * 7/2002 Shaffer ....................... 604/263
2003/0032922 A1 * 2/2003 Moorehead ................. 604/110
2004/0194272 A1 * 10/2004 Roberts ....................... 29/254

* cited by examiner

*Primary Examiner*—Yvonne R. Abbott
(74) *Attorney, Agent, or Firm*—Law Office of Timothy E. Siegel; Timothy E. Siegel

(57) ABSTRACT

A method of removing a dart from an animal body. The method uses a dart removal facilitating tool that includes a handle, adapted to be grasped by a human hand. A dart removal head is attached to the handle and is adapted to be placed in proximity to the dart. The head has a surface that is adapted to be pressed against animal flesh without creating further injury. The method includes pressing the dart removal head against a portion of the animal body near the dart and engaging for dart for removal from the animal body while the dart removal head is being pressed against the portion of the animal body.

12 Claims, 4 Drawing Sheets

METHOD OF REMOVING A STUN GUN DART

BACKGROUND OF THE INVENTION

The proliferation of stun guns among law enforcement, security forces and facilities for holding large animals throughout the world, has caused an unanticipated problem. Stun guns, such as the Taser® gun, work by shooting barbed darts into the subject. These darts are connected to thin wires, through which a series electric pulses is passed to pacify the subject.

After the subject has been subdued, it is necessary for a responding professional to remove the dart(s) from the subject. This is typically done by holding the subject down with one hand, while removing the dart with the other. Unfortunately, during this operation the subject may suddenly move in an effort to gain freedom. This, in turn, may throw the responding professional off balance to the point that he inadvertently jabs the barbed end of the newly removed dart into the hand used to stabilize the body part that had received the dart.

Far from being a minor, temporary injury, this brief event may have a life-long and tragically life-shortening effect on the responding professional, who may contract hepatitis, HIV or any one out of a long list of blood born pathogens from blood on the dart. This very occurrence has become all too common, with thousands of people all infected with a deadly virus through this mechanism or a related cause, such as an intra venous needle stick. Some way must be found to make the removal of stun gun darts safer for the personnel who must remove them from the subjects.

SUMMARY OF THE INVENTION

In a first, separate aspect, the present invention is a method of removing a dart from an animal body. The method uses a dart removal facilitating tool that includes a handle, adapted to be grasped by a human hand. A dart removal head is attached to the handle and is adapted to be placed in proximity to the dart. The head has a surface that is adapted to be pressed against animal flesh without creating further injury. The method includes pressing the dart removal head against a portion of the animal body near the dart and engaging the dart for removal from the animal body while the dart removal head is being pressed against the portion of the animal body.

In a second separate aspect, the present invention is a dart removal facilitating tool, comprising a handle, adapted to be grasped by a human hand and a dart removal head, attached to the handle. The head has a pair of ears, each of which has a substantially flat under surface adapted to be pressed against animal flesh without creating further injury. The ears are adapted to be placed about the dart for restraining the animal body during dart removal.

In a third separate aspect, the present invention is a subject engaging tool, which includes a handle, adapted to be grasped by a human hand and having an illumination assembly adapted to shine light through a translucent end of the handle. A body engaging portion is detachably attached to the handle, and is made of translucent material for accepting light from the handle illumination assembly and for communicating the light to a desired illumination area.

The foregoing and other objectives, features and advantages of the invention will be more readily understood upon consideration of the following detailed description of the preferred embodiment(s), taken in conjunction with the accompanying drawings.

DETAILED DESCRIPTION OF THE PREFERRED EMBODIMENT(S)

Figure 1:
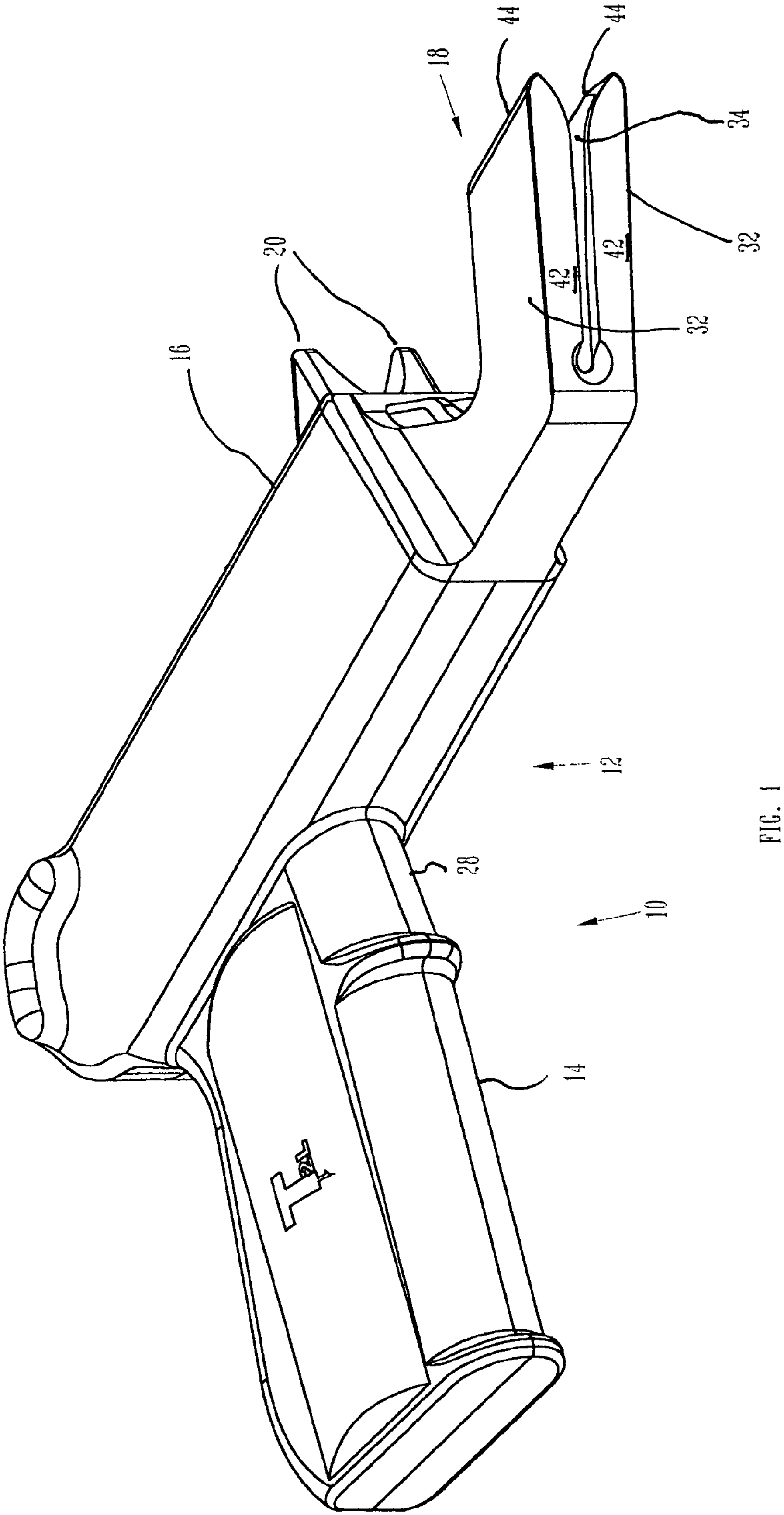
FIG. 1 is a perspective view of a dart removal tool according to the present invention.
Figure 2:
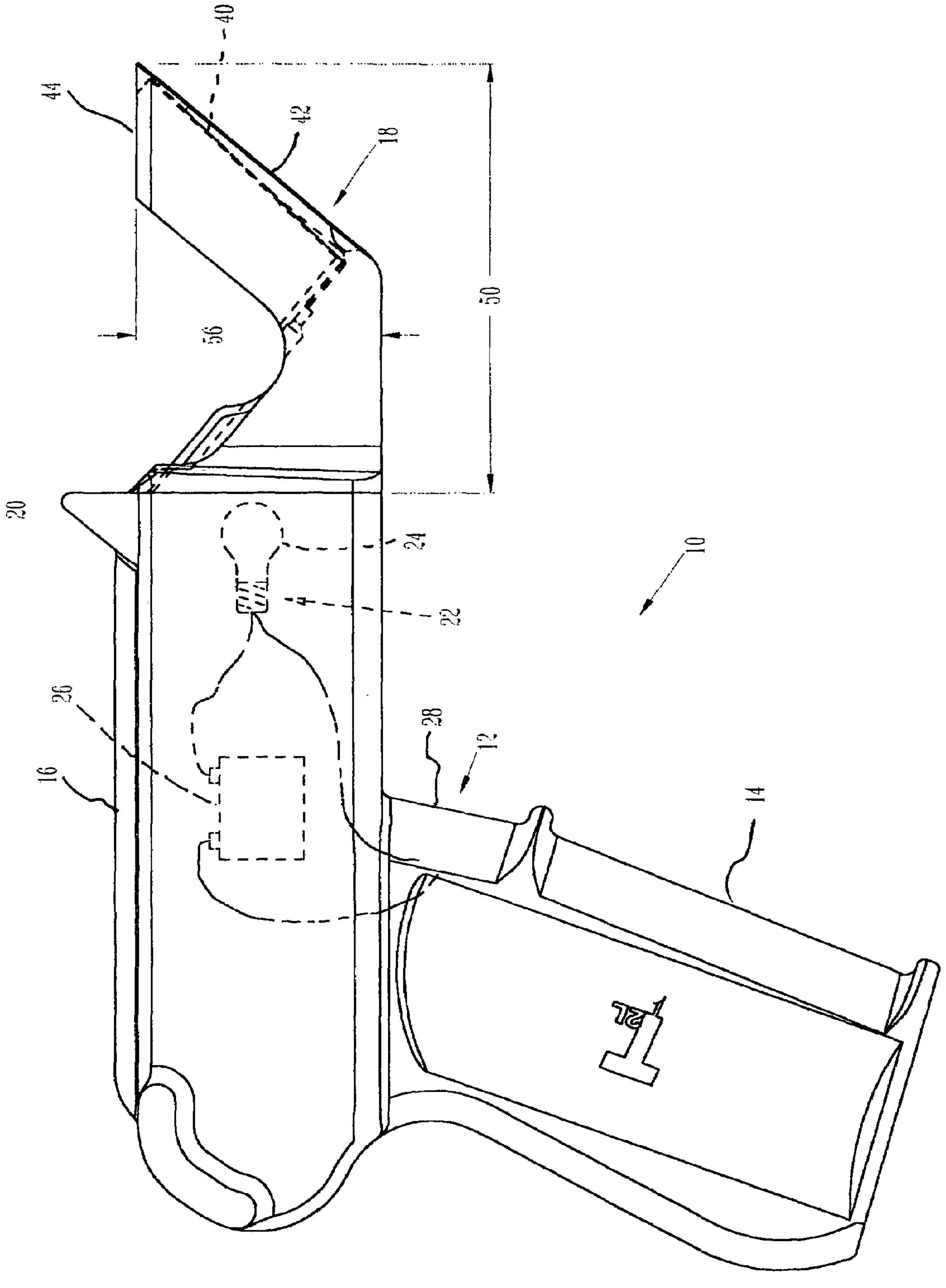
FIG. 2 is a side view of the dart removal tool of FIG. 1.

Referring to FIGS. 1 and 2, one preferred embodiment of a dart removal tool 10 according to the present invention includes handle 12, which in turn includes a hand grip 14 and a spacer 16. Detachably supported at the end of spacer 16 that is furthest from hand grip 14 is a dart removal head 18. Spacer 16 also includes a sight 20, adapted to facilitate a user in aligning tool 10 with a dart.

In addition, spacer 16 incorporates a lighting system 22 (FIG. 2), that includes a light emitting diode (LED) 24 and a battery 26. System 22 is electrically connected to and activated by a manually actuated switch 28. The end of spacer 16 that mates with head 18 is transparent, thereby permitting light from LED 24 to shine into head 18, which is made of translucent material.

Figure 3:
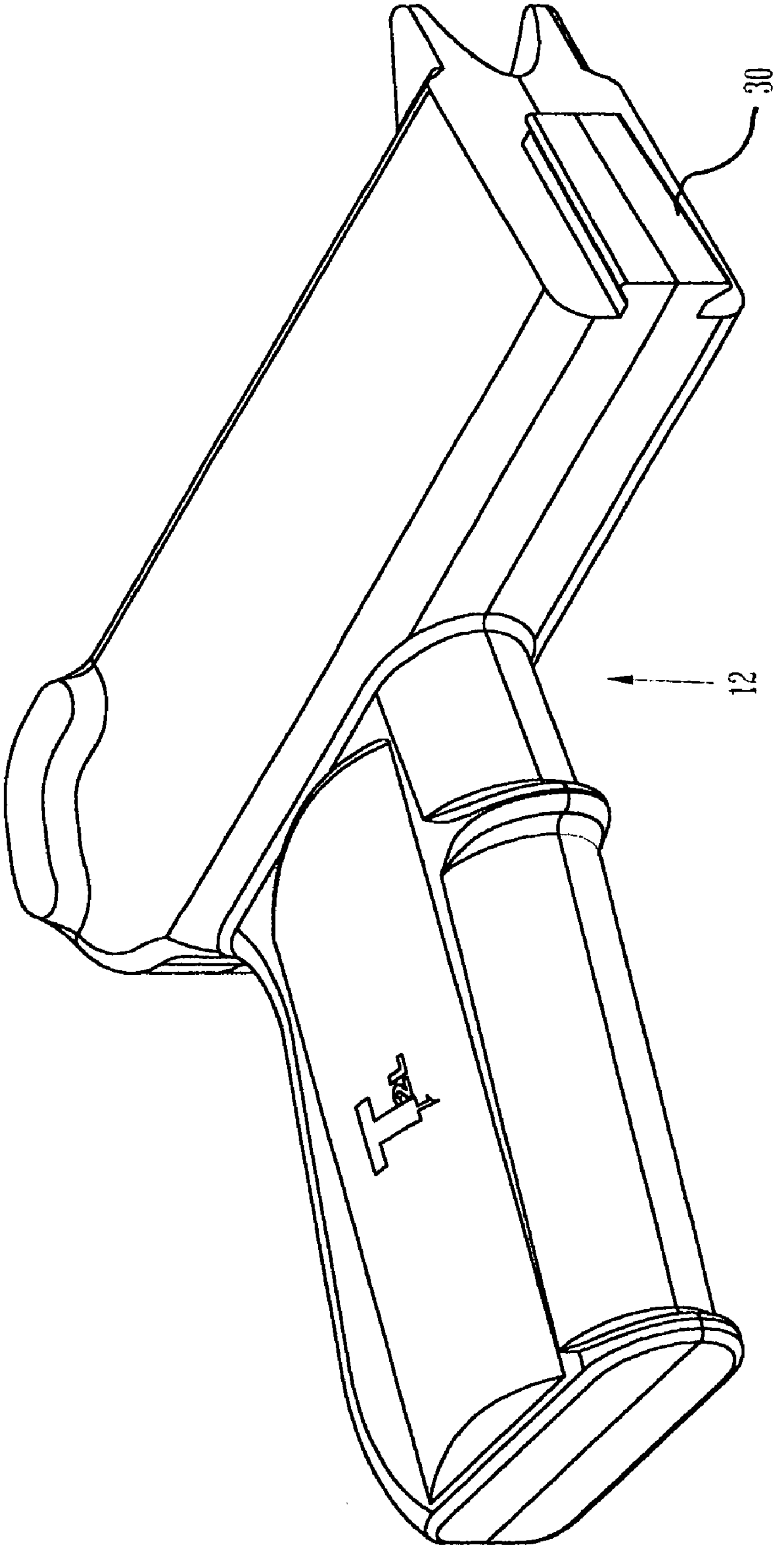
FIG. 3 is a perspective view of the handle of the dart removal tool of FIG. 1.
Figure 4:
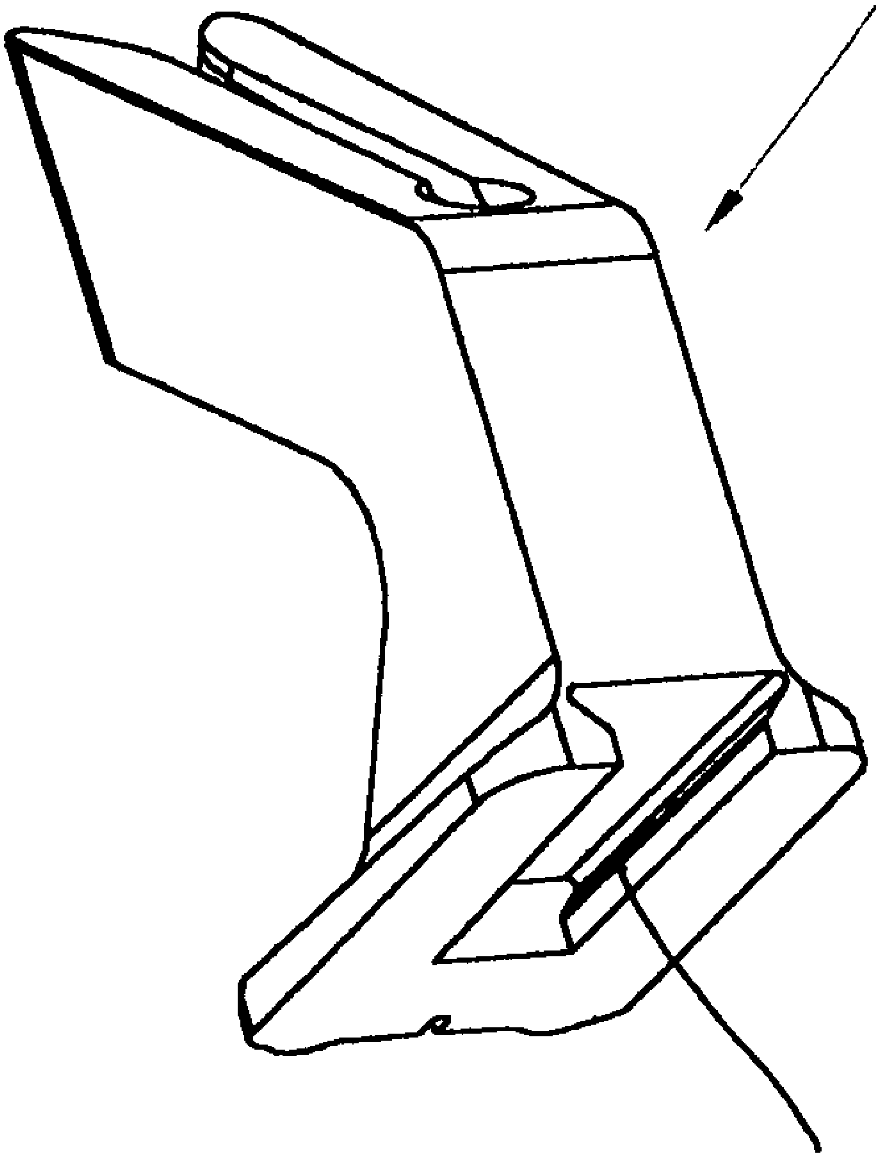
FIG. 4 is a perspective view of the head of the dart removal tool of FIG. 1.

In greater detail, head 18 is made light weight polycarbonate material and is detachably connected to spacer 16 by a mating dovetail key 30 and groove 31 combination (FIGS. 3 and 4). A pair of ears 32 define a slot 34 (FIG. 1) adapted to engage a dart. Ears 32 and slot 34 may be considered a dart engagement portion. Referring to FIG. 2, an internal surface 40 of each ear 32, has a different slope than front surface 42, so that each ear 32 is in the form of a wedge, adapted to pull out a dart. In addition, the top surface 44 of each ear is made of roughened polymer material, thereby permitting light to escape more easily and to illuminate the area directly in front of surfaces 44.

The method of use and advantages of 10 may now be evident. A responding professional can hold tool 10 by hand grip 14 and guide it toward an embedded dart using sight 20 and the illumination provided by assembly 22. After guiding ears 32 so that dart is in slot 34, the professional may simply slide head 18 forward, so as to cause the wedge shape of each ear 32 to remove the dart. Accordingly, there is no need for the hand of the professional to touch the dart during the removal process. It is also within the scope of the method of the invention, however, for the professional to use tool 10 to restrain the part of the subject near the dart, and use his free hand to remove the dart.

Handle 14 is sized to fit comfortably in a human hand. Preferred embodiments exist with various handle sizes, to accommodate different sized hands. Spacer 16 may be of any length from 2 cm to 40 cm depending on the desired trade-off between maintaining a safe distance to the dart being removed, versus better control of the dart removal head 18. In one preferred embodiment spacer 16 has a user adjustable length. The length 50 of head 18 is preferably 7.2 cm (2.8 in) and its height 56 (FIG. 2) is preferably 4.1 cm (1.6 in).

Because tool 10 can both hold the subject down and remove the dart, it permits the responding professional to avoid using one hand to hold the subject down while the dart is removed with the other hand. As noted in the background, it is the hand used to hold the subject down that is likely to be stuck by the dart, as the dart is removed. Even if the professional does use his free hand to remove the dart, however, the hand holding tool 10 is further from the subject at the moment when the dart is remove than it would otherwise be, and is therefore safer from a chance dart puncture.

In the context of this application, a human body is a type of animal body.

The terms and expressions that have been employed in the foregoing specification are used as terms of description and not of limitation. There is no intention, in the use of such terms and expressions, of excluding equivalents of the features shown and described or portions thereof, it being recognized that the scope of the invention is defined and limited only by the claims which follow.

The invention claimed is:

1. A method of removing a stun gun dart from the body of a human suspect, while avoiding becoming contaminated by a dart puncture wound, comprising:

(a) providing a dart removal facilitating tool, including:
   (i) a handle, adapted to be grasped by a human hand; and
   (ii) a dart removal head, attached to said handle and having a pair of ears for placement about said dart, each said ear having a surface area of greater than a square centimeter so that it can be pressed against human flesh without creating further injury;
(b) pressing said dart removal head against a portion of said human body near said dart, thereby constraining potential movement on part of said human suspect; and
(c) engaging said dart for removal from said human body while said dart removal head is being pressed against said portion of said human body, thereby constraining movement of said human suspect and avoiding being thrown off balance by sudden movement and puncturing oneself with said stun gun dart as a result.

2. The method of claim 1 wherein said handle includes a bend, adapted to permit a user to contact said dart removal facilitation tool to said animal body, while keeping his wrist straight.

3. The method of claim 2 wherein said bend has an included angle of approximately 100°.

4. The method of claim 2 wherein said dart removal head is removable from said handle.

5. The method of claim 4 wherein said dart removal head is attached to said handle by means of a mating dovetail key and groove.

6. The method of claim 1 wherein said are spaced apart laterally closely enough to engage one of said darts in a space defined between said ears and wherein said ears can be used to pull said dart out of said human suspect, thereby avoiding close contact with said dart, and thereby avoiding the possibility of self puncture by said dart.

7. The method of claim 1 wherein said dart removal head is removable from said handle.

8. The method of claim 7 wherein said ears are each in the form of a wedge, and wherein said dart is pulled from said subject by moving said ears forward so as to remove said dart by way of wedge action.

9. The method of claim 7 wherein said dart removal head is attached to said handle by means of a mating dovetail key and groove.

10. The method of claim 1 wherein said dart removal head is made of polycarbonate material.

11. The method of claim 1 wherein said dart removal head is translucent.

12. The method of claim 11 wherein said dart removal head is controllably illuminated.

* * * * *